United States Patent [19]

Biere et al.

[11] Patent Number: 4,952,698
[45] Date of Patent: Aug. 28, 1990

[54] IMIDAZOLE DERIVATIVES

[75] Inventors: Helmut Biere; Andreas Huth; Dieter Rahtz; Ralph Schmiechen; Dieter Seidelmann; Herbert H. Schneider; David N. Stephens, all of Berlin, Fed. Rep. of Germany

[73] Assignee: Schering Aktiengesellschaft, Berlin, Fed. Rep. of Germany

[21] Appl. No.: 189,511
[22] PCT Filed: Jul. 30, 1987
[86] PCT No.: PCT/DE87/00342
 § 371 Date: Apr. 11, 1988
 § 102(e) Date: Apr. 11, 1988
[87] PCT Pub. No.: WO88/01268
 PCT Pub. Date: Feb. 25, 1988

[30] Foreign Application Priority Data

Aug. 11, 1986 [DE] Fed. Rep. of Germany ....... 3627155

[51] Int. Cl.$^5$ .................. C07D 233/90; C07D 413/04
[52] U.S. Cl. ..................................... 548/131; 548/343
[58] Field of Search ................................ 548/131, 343

[56] References Cited

U.S. PATENT DOCUMENTS 4,292,431 9/1981 Kim ....................................... 548/342
4,755,213 7/1988 Schmierer ............................... 71/92
4,780,539 10/1988 Watjen ................................. 548/131

OTHER PUBLICATIONS

Chemical Abstracts Registry No. 18075-64-4 (1978).
Goderol, J. Med. Chem. 8, 220 (1965).
Ktritzky Comprehensive Heterocyclic Chemistry vol. 5, p. 468 (1952).

Primary Examiner—Robert Gerstl
Attorney, Agent, or Firm—Millen, White & Zelano

[57] ABSTRACT

Imidazole derivatives of general formula I

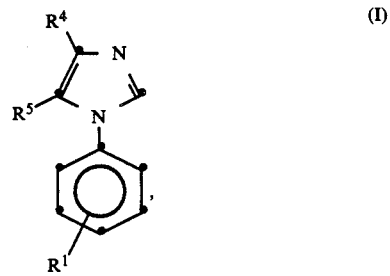

wherein
$R^1$ represents hydrogen or halogen in the o-, m- or p-position, and the halogen can occur once or repeatedly in the phenyl radical,
$R^4$ represents

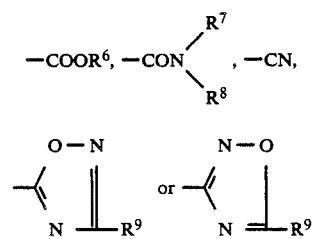

with $R^6$ and $R^9$ representing hydrogen or a straight or branched alkyl group with 1 to 6 carbon atoms, $R^7$ and $R^8$ are the same or different and represent hydrogen or a straight or branched alkyl group with 1 to 6 carbon atoms or $R^7$ and $R^8$ together with the nitrogen atom represent a saturated heterocyclic five-membered or six-membered ring optionally containing another heteroatom, and
$R^5$ represents hydrogen, an alkyl group with 1 to 6 carbon atoms or an alkoxyalkyl group with 1 to 6 carbon atoms, which are suitable as psychopharmaceuticals, are described.

6 Claims, No Drawings

IMIDAZOLE DERIVATIVES

The invention relates to new CNS active imidazole derivatives of general formula I

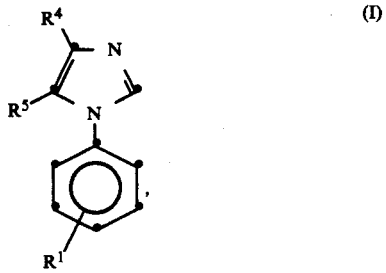

wherein $R^1$ represents hydrogen or halogen in the o-, m- or p-position, and the halogen can occur once or repeatedly in the phenyl radical, $R^4$ represents

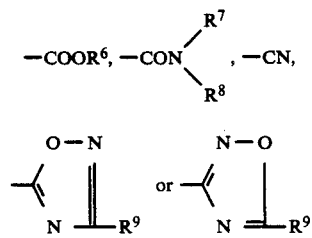

with $R^6$ and $R^9$ representing hydrogen or a straight or branched alkyl group with 1 to 6 carbon atoms, $R^7$ and $R^8$ are the same or different and represent hydrogen or a straight or branched alkyl group with 1 to 6 carbon atoms or $R^7$ and $R^8$ together with the nitrogen atom represent a saturated heterocyclic five-membered or six-membered ring optionally containing another heteroatom, and $R^5$ represents hydrogen, an alkyl group with 1 to 6 carbon atoms or an alkoxyalkyl grop with 1 to 6 carbon atoms.

By halogen is understood fluorine, chlorine, bromine or iodine, with fluorine and chlorine being preferred.

By alkyl is meant in each case a straight or branched alkyl grop with 1 to 6 carbon atoms, for example, the methyl, ethyl, propyl, isopropyl, butyl, pentyl and hexyl group. $C_{1-4}$ alkoxy $C_{1-4}$ alkyl, especially $C_{1-4}$ alkoxymethyl is to be regarded as preferred embodiment for $R^5$ in the meaning of alkoxyalkyl.

If $R^7$ and $R^8$ together with the nitrogen atom represent a saturated heterocyclic five-membered or six-membered ring optionally containing another heteroatom,

for example, stands for pyrrolidine, piperidine, morpholine or piperazine.

It is known that certain sites in the central nervous system of vertebrates exhibit a high specific affinity for the binding of 1,4- and 1,5-benzodiazepines (Squires, R. F. and Braestrup, C., Nature (London) 266 (1977) 734). These sites are called benzodiazepine receptors.

It has been found that the substituted imidazole derivatives according to the invention, although they differ greatly from benzodiazepines in their chemical structure, surprisingly exhibit a great affinity and specificity for binding on the benzodiazepine receptors and at the same time only slight toxicity.

Thus, the compounds according to the invention can, for example, have agonistic, inversely agonistic and antagonistic effects on the known properties of benzodiazepines. Benzodiazepines, for example, exhibit anticonvulsive, anxiolytic and muscle-relaxing as well as sedating effects.

A disadvantage of the benzodiazepines is the relatively broad activity spectrum with slight selectivity.

Therefore, as before there exists a need for well tolerated substances with dissociated CNS effectiveness.

The compounds according to the invention on the basis of their biological effectiveness appear to be suitable as psychopharmaceuticals for human medicine. They can be formulated for psychopharmaceutical preparations, for example, for oral and parenteral application.

As formulation auxiliary agents physiologically tolerable organic and inorganic vehicles, which are inert toward the compounds according to the invention, are suitable.

As vehicles there can be mentioned, for example, water, salt solutions, alcohols, polyethylene glycols, polyhydroxyethoxylated castor oil, gelatins, lactose, amylose, magnesium stearate, talc, silicic acid, fatty acid mono- and di-glycerides, pentaerythritol fatty acid ester, hydroxymethylcellulose and polyvinyl pyrrolidone.

The pharmaceutical preparations can be sterilized and/or mixed with auxiliary agents, such as lubricants, preservatives, stabilizers, wetting agents, emulsifiers, buffering agents and dyes.

For parenteral application especially injection solutions or suspensions, particularly aqueous solutions of the active compounds in polyhydroxyethoxylated castor oil are suitable. Surfactant auxiliary agents such as salts of bile acids or animal or vegetable phospholipids, but also mixtures of them as well as liposomes and their components can also be used as vehicles.

Especially tablets, dragees or capsules with talc and/or a hydrocarbon vehicle or binder, such as, for example, lactose, corn or potato starch are suitable for oral application. The application can also take place in liquid form such as, for example, juice to which optionally a sweetener is added.

The compounds according to the invention are offered in a dosage unit of 0.05 to 10 mg of active substance in a physiologically tolerable vehicle.

The compounds according to the invention are used in a dose of 0.1 to 300 mg/day, preferably 1–30 mg/day.

Production of the compounds according to the invention of general formula I takes place by the fact that an aniline of general formula II

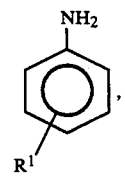

wherein
$R^1$ has the meaning indicated in formula I, is reacted with a 2-azabutadiene of general formula III

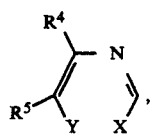 (III)

wherein $R^4$ and $R^5$ have the meaning indicated in formula I and X and Y represent leaving groups, in the presence of acids at temperatures from 0° to 150° C., and optionally an ester group present in the molecule is transesterified or saponified, a free carboxyl group optionally is esterified, amidated or reacted with an amidoxime of the formula $R^9$—C(=NOH)NH$_2$ to the 5-oxadiazolyl derivative, and optionally a nitrile group present in the molecule is hydrolyzed to the carbonyl amide or carboyl group or converted by the imino ester group into the ester group (COOR$^6$) or with hydroxyl amine by the amidoxime and then with an alkane carboxylic acid of formula $R^9$—COOH or an activated derivative of the acid into the 3-oxadiazolyl derivative.

The reaction according to the invention of anilines of formula II with 2-azabutadienes of formula III to imidazole derivatives of formula I takes place in the presence of acids at temperatures of 0° to 150° C. Especially dialkylamines, such as dimethylamine and diethylamine, and cyclic amines, such as pyrrolidine, are suitable as leaving groups X and Y.

For example, the reaction is so performed that the aniline derivative and the azabutadiene are first stirred in an organic acid, such as, for example, formic acid, acetic acid, propionic acid or trifluoroacetic acid, first at room temperature and then heated up to the boiling point of the reaction mixture (to about 120° C.)

The acid can serve simultaneously as reaction agent and also as solvent. But also solvents such as, for example, alcohols, ethers, ketones, esters such as ethyl acetate, hydrocarbons such at toluene, or halogenated hydrocarbons such as carbon tetrachloride can be added.

The amount of acid can vary in broad limits, but it is used in excess. A 3-10-fold acid excess, relative to the aniline and azabutadiene, is preferably selected.

The molar ratios of aniline and azabutadiene are not critical for the success of the reaction. In general, approximately equal molar amounts of the reactants are used, and molar amounts of 1 of aniline and 1.1 azabutadiene are preferred. The reaction according to the invention can basically be performed also in solvents indicated above with catalytic amounts of mineral acids, such as sulfuric acid, hydrochloric acid, perchloric acid or p-toluenesulfonic acid.

The surprising advantage of the process according to the invention is in the chemoselective synthesis of imidazole derivatives with the formation of an isomer in a single process step.

For the optionally subsequent transesterification, all usual methods are suitable. There can be mentioned, for example, the reaction of carboxylic acid ester with the corresponding alcohol in the presence of the alcoholate or with the corresponding alcohol with titanium tetraalcoholate or with the alcohol in the presence of an acid. The transesterification is performed at temperatures from about 0° to 120° C.

The optionally subsequent saponification of the ester group suitably takes place in an alkaline manner, in which the ester is refluxed in dilute aqueous lye, such as potassium or sodium hydroxide.

Esterification of the carboxyl group takes place in a way known in the art with the corresponding alcohol in acid or in the presence of an activated acid derivative. Acid chloride, imidazolide or anhydride, for example, are suitable as activated acid derivatives.

For amidation the imidazole-4-carboxylic acid or the corresponding ester, with the help of N,N'-carbonyldiimidazole or dicyclohexylcarbodiimide, is reacted with a primary or secondary amine of general formula.

The reaction can also take place in a way known in the art by activated acid derivatives such as by anhydride or anhydride mixed with chloroformic acid ester. The amidation is usually performed in an aprotic solvent such as dimethylformamide, tetrahydrofuran, toluene or methylene chloride at temperatures from about 0° to 100° C.

For introduction of the 5-oxadiazolyl radical, the imidazole-4-carboxylic acid with an amidoxime of the formula $R^9$—C(—NOH)NH$_2$, in which $R^9$ has the meaning indicated in formula I, in an inert solvent at room temperature is brought for condensation to the boiling point of the reaction mixture. Toluene and dimethylformamide, for example, are suitable as inert solvents. Before the condensation reaction the free carboxylic acid is usefully activated in a suitable way. For this purpose, the free acid can be converted into the mixed anhydride, into the activated ester or into the chloride. Activation with imidazole/thionyl chloride in an aprotic solvent such as dioxane, tetrahydrofuran, dimethylformamide or N-methylpyrrolidone at temperatures between 0° and 50° C. has proved worthwhile.

The optionally subsequent modification of the nitrile group can be performed according to known methods. For example, the nitrile group can be converted by acid or alkaline hydrolysis into the carbonyl amide or carboxyl group or with the corresponding alcohol with addition of hydrochloric acid gas by the imino ester group into the ester group.

For introduction of the 3-oxadiazolyl radical the imidazole-4-carbonitrile is reacted in a way known in the art with hydroxylamine to amidoxime and then condensed with an alkane carboxylic acid of formula $R^9$-COOH, in which $R^9$ has the meaning indicated in formula I, or with an activated derivative of the acid in an inert solvent The condensation is performed in the same way as in the case of the 5-oxadiazolyl compound.

The anilines of general formula II and 2-azabutadienes of general formula III, used as initial materials, are known for the most part or can be produced according to known methods.

2-Azabutadienes are described, for example, in Liebigs Ann. Chem. 1980, 344 and in DE-OS 29 19 891.

Production of the new 2-azabutadienes 2-4, used in the examples, is explained by the following examples.

Azabutadiene 1:

1,4-Bis(dimethylamino)-2-aza-1,3-butadiene-3-carboxylic acid ethyl ester

According to Liebigs Ann. Chem. 1980, 344.

Azabutadiene 2:

1,4-Bis(dimethylamino)-3-(3-ethyl-1,2,4)-oxadiazol-5-yl)-2-aza-1,3-butadiene

A mixture of 11.5 g of 5-aminomethyl-3-ethyl-1,2,4-oxadiazole and 24 ml of dimethylformamide dimethyl acetal is heated to 80° C. for 7 hours; in doing so, 10 ml of the resulting methanol is distilled off. After addition of another 12 ml of DMF acetal the mixture is refluxed for 3 hours, then fractionated. The fraction coming over (azabutadiene 2) is obtained in a yield of 72% ($n_D^{20}$ 1.5908) at 155°–160° C. and 0.03 torr.

Production of the initial compound takes place as follows:

(a) 3-Ethyl-5-(phthalimidomethyl)-1,2,4-oxadiazole

A suspension of 26.0 g of carbonyldimidazole in 250 ml of THF is added to a solution of 65.7 g of phthalimidoacetic acid in 500 ml of tetrahydrofuran (THF) (abs.) at 40° C. After about 1 hour, no generation of gas can be detected any longer. A solution of 28.2 propioamidoxime in 50 ml of THF is now added and stirred for 24 hours at room temperature. After filtering off of the precipitate the filtrate is concentrated in a vacuum and refluxed on a water separator for 6 hours after addition of 500 ml of dry xylene. The still hot solution is separated from the oily residue and concentrated in a vacuum. After crystallization from ethanol, 31.5 g of phthalimide with a melting point of 106–107° C. (76.5% relative to carbonyldiimidazole) is obtained.

(b) 5-Aminomethyl-3-ethyl-1,2,4-oxadiazole

A suspension of 32.2 g of phthalimide in 250 ml of methanol is mixed with 4.5 g (140 mmol) of hydrazine at room temperature, and the substance quickly dissolves. The reaction mixture is refluxed for 3 hours, then the resulting precipitate is suctioned off, rewashed with methanol and the filtrate is concentrated. After suspending of the residue with diethyl ether is again filtered, concentrated and the oil is distilled on a bulb tube: boiling point 90°–100° C. (at 0.03 torr).

Yield: 14.87 g (91.6%): $n_D^{20}$ 1.4691.

Azabutadiene 3:

1,4-Bis(dimethylamino-3-cyano-2-azabutadiene

A mixture of 45 g of aminoacetonitrile and 190 g of dimethylformamide dimethyl acetal is first heated, with exclusion of moisture, for 4 hours at 100° C. (bath temperature), then for 3 hours to 120° C. In doing so, about 90 ml of a more volatile component (methanol) is distilled off, 100 ml of DMF dimethyl acetal is again added and heated for another 5 hours to 150° C. (bath temperature). After the subsequent fractionating there are obtained:

Fraction 1:
(Boiling point 64°–74° C./0.04 torr): 59.9 g (67.4%) of dimethylaminomethyleneaminoacetonitrile.

Fraction 2:
(Boiling point 115°–125° C./0.03 torr); 31 g (23.3%) of the title compound.

The title compound is crystallized from hexane.
Melting point: 78°–81° C.

Azabutadiene 4:

3-Cyano-1-dimethylamino-4-pyrrolidino-2-aza-1,3-pentadiene

A mixture of 22 g of dimethylaminomethylene-aminoacetonitrile, 27 g of dimethyl acetamide dimethyl acetal and 14 g of pyrrolidine is heated for 48 hours to 80° C. (bath temperature). After concentration in a vacuum and subsequent bulb tube distillation (160°–185° C./0.08 torr), 30 g of the title compound is obtained, which is crystallized from hexane.

Melting point: 49°–530° C. (E,Z mixture).

Azabutadiene 5

1-dimethylamino-3-(3-ethyl-,1,2,4-oxadiazol-5-yl)-4-pyrrolidino-2-azapenta-1,3-diene (E,Z)

(a) A mixture of 26 g of 5-aminomethyl-3-ethyl-1,2,4-oxadiazole and 30 ml of dimethylformamide dimethyl acetal is heated to 80° C. for 6.5 hours.

Then 16 ml of methanol is distilled off and the resulting product is purified by bulb tube distillation. 27.9 g (74.8%) of 3-ethyl-5-(N-dimethylaminomethylene-aminomethyl)-1,2,4-oxadiazole is obtained.

Boiling point: 130°–150° C./0.05 torr: $n_D^{20}$ 1.4924.

(b) 13.6 g of the product obtained under a, 15.0 g of dimethyl acetamide dimethyl acetal and 8.0 g of pyrrolidine are heated for 21 hours under nitrogen to 80° C. Then the resulting alcohol is distilled off and the reaction product is purified by bulb tube distillation. 15.4 g of a fraction, which comes over at 215°–230° C./0.04 torr, is obtained. By recrystallization from n-hexane 9.5 g (45.7%) of the title compound with a melting point of 59°–62° C. is obtained.

Azabutadiene 6

1-dimethylamino-3-(3-ethyl-1,2,4-oxadiazol-5-yl)-5-methoxy-4-(1-pyrrolidinyl)-2-azapenta-1,3-diene (E,Z)

(a) Methoxy acetic acid dimethylamide dimethylacetal 42.2 g of methoxy acetic acid dimethylamide in three portions is added to 53.4 g of trimethyloxonium tetrafluoroborate with cooling. The reaction mixture is then stirred for 2 hours at room temperature and then allowed to stand overnight. After dissolving in 40 ml of dichloromethane the resulting salt is slowly added to a solution of sodium methoxide in methanol (produced by dissolution of 10.4 g of sodium in 225 ml of methanol). Then it is stirred for 2 hours at room temperature. For working up, the resulting precipitate is suctioned off and washed with a little ethanol. After the distilling off of the solvents, the filtrate forms 2 phases. By bulb tube distillation 9.08 g (15%) of the desired product is obtained from the above phase.

Boiling point: 54°–57° C./14 torr: $n_D^{20}$: 1.4204

(b) 8.8 g of the product produced under (a) is reacted with 6.6 g of 3-ethyl-5-(N-dimethylaminomethylene-aminomethyl)-1,2,4-oxadiazole and 4.5 ml of pyrrolidine similar to the production of azabutadiene 5. By bulb tube distillation 11.8 g (11%) of azabutadiene 6 is obtained.

Boiling point: 200°–240° C./0.05 torr..

EXAMPLE 1

(a) 1,3-chlorophenyl)-imidazole-4-carboxylic acid ethyl ester 2.2 g of azabutadiene 1, with cooling, is instilled in 8 ml of glacial acetic acid and then mixed with 1 g of 3-chloroaniline. The mixture is first stirred for 30 minutes at room temperature, then heated for 5 hours to 80° C. (bath temperature). After working up with sodium hydrogen carbonate solution the crystalline residue is recrystallized from diisopropyl ether. 1.63 g of the title compound (81% relative to chloroaniline) is obtained.

Melting point: 104°–105° C.

Similarly to example 1(a) there are obtained:
(b) 1-(3,4-dichlorophenyl)-imidazole-4-carboxylic acid ethyl ester from 3,4-dichloroaniline
(c) 1-(4-chlorophenyl)-imidazole-4-carboxylic acid ethyl ester from 4-chloroaniline
(d) 1-(4-fluorophenyl)-imidazole-4-carboxylic acid ethyl ester from 4-fluoroaniline.

EXAMPLE 2

(a) 1-(3-chlorophenyl)-imidazole-4-carboxylic acid isopropyl ester

A solution of 0.4 g of 1-(3-chlorophenyl)-imidazole-4-carboxylic acid ethyl ester in 40 ml of i-propanol is mixed with 0.5 ml of titanium tetraisopropanolate and refluxed for 8 hours. After concentration of the solution, it is filtered over silica gel and recrystallized from diisopropyl ether. 267 mg (63%) of the title compound with a melting point of 109° C. is obtained from diisopropyl ether.

In a similar way there is produced:

(b) 1-(4-fluorophenyl)-imidazole-4-carboxylic acid isopropyl ester

EXAMPLE 3

(a) 1-(3-chlorophenyl)-imidazole-4-carboxylic acid

A suspension of 1 g of 1-(3-chlorophenyl)-imidazole-4-carboxylic acid ethyl ester in 10 ml of 2N KOH is heated to 110° C. (bath temperature) for 2 hours. After cooling, it is acidified to pH 3–4 with 4N HCl and the precipitate is recrystallized from i-propanol. 0.73 (82%) with a melting point of 195° C. is obtained.

In a similar way there is obtained:

(b) 1-(4-fluorophenyl)-imidazole-4-carboxylic acid

EXAMPLE 4

(a) 1-(3-chlorophenyl)-imidazole-4-carboxylic acid diethylamide 0.5 g of N,N'-carbonyldiimidazole in 5 ml of DMF is instilled in a solution of 0.56 g of acid (Example 3(a)) in 10 ml of dimethylformamide, then the solution is heated for 30 minutes to 60° C. to the completed generation of gas and then mixed with 1.3 ml of diethylamine. The mixture is heated for 2 hours to 90° C., then concentrated in a vacuum and precipitated with water. The raw product is crystallized from diisopropylether. 0.48 g (70%) of the title compound with a melting point 105° C. from diisopropylether is obtained.

In a similar way is obtained:

(b) 1-(4-fluorophenyl)-imidazole-4-carboxylic acid diisopropylamide

EXAMPLE 5

(a) 1-(3-chlorophenyl)-4-(3-ethyl-1,2,4-oxadiazol-5-yl)-imidazole

The production takes place from 3-chloroaniline and azabutadiene 2 similarly to Example 1(a). 60% with melting point of 134°–135° C. (ethyl acetate) is obtained.

In a similar way, the corresponding anilines are obtained:
(b) 1-(3,4-dichlorophenyl)-4-(3-ethyl-1,2,4-oxadiazol-5-yl)-imidazole
(c) 1-(4-chlorophenyl)-4-(3-ethyl-1,2,4-oxadiazol-5-yl)-imidazole
(d) 1-(4-fluorophenyl)-4-(3-ethyl-1,2,4-oxadiazol-5-yl)-imidazole
(e) 1-(3-bromophenyl)-4-(3-ethyl-1,2,4-oxadiazol-5-yl)-imidazole

EXAMPLE 6

(a) 1-(3-chlorophenyl)-imidazole-4-carbonitrile

The production takes place from 3-chloroaniline and azabutadiene 3 similarly to Example 1(a). Besides 25% of 1-(3-chlorophenyl)-imidazole-4-carboxylic acid amide, 35% of the title compound is obtained after chromatography.

EXAMPLE 7

(a) 1-(3-chlorophenyl)-5-methyl-imidazole-4-carbonitrile

The production takes place from 3-chloroaniline and azabutadiene 4 similarly to Example 1(a). 30% of the title compound is obtained after chromatography on silica gel.

Melting point: 117°–118° C. from diisopropyl ether and similar to 7a as by-product.

(b) 1-(3-chlorophenyl)-5-methyl-imidazole-4-carboxylic acid amide

Melting point: 179°–181° C. (ethyl acetate) with 3.4% yield.

In a similar way it obtained (c) 1-(4-fluorophenyl)-5-methyl-imidazole-4-carbonitrile

EXAMPLE 8

(a) 1-(3-(chlorophenyl)-4-(5-ethyl-1,2,4-oxadiazol-3-yl)-5-methyl imidazole 653 mg of 1-(3-chlorophenyl)-5-methyl-imidazole-4carbonitrile from example 7(a), 695 mg of hydroxylammonium chloride and 690 mg of potassium carbonate are heated in 32 ml of ethanol for 1.5 hours to 110° C. Then it is concentrated, the residue is stirred with water and the resulting solid is suctioned off. After drying, it is recrystallized from ethanol.

Yield: 600 mg (79.8%) of 1-(3-chlorophenyl)-5-methyl-imidazole-4-formamidoxime with a melting point of 206°–209° C.

(b) 577 mg of the formamidoxime obtained under 8(a) is placed in 40 ml of anhydrous tetrahydrofuran and is cardfully mixed with 283 mg of propionyl chloride. Then it is stirred for 16 hours at room temperature. After the tetrahydrofuran has been distilled off, the residue is taken up in 25 ml of xylene and the batch is refluxed for 3.5 hours. After concentraion and chromatography of the raw product on silica gel with toluene/ethyl acetate (1:1), 0.74 g of 1-(3-chlorophenyl)-4-(5-ethyl-1,2,4-oxadiazol-3-yl)-5-methyl imidazole is obtained.

Melting point: 71°-72° C. (diisopropyl ether).

EXAMPLE 9

1-(3-chlorophenyl)-4-(3-ethyl)-1,2,4-oxadiazol-5-yl)-5-methyl-imidazole

Production takes place from 3-chloroaniline and azabutadiene 5 similarly to Example 1(a). After chromatography on silica gel, 31.7% of the title compound is obtained.

Melting point: 96°-97° C. (diisopropyl ether).

EXAMPLE 10

1-(3-chlorophenyl)-4-(3-ethyl-1,2,4-oxadiazol-5-yl)-5-methoxymethyl-imidazole

Production takes place from 3-chloroaniline and azabutadiene 6 similarly to Example 1(a). After chromatography on silica gel, 46% of the title compound is obtained.

Melting point: 125°-126° C. (diisopropyl ether/ethanol).

We claim:
1. An imidazole of the formula

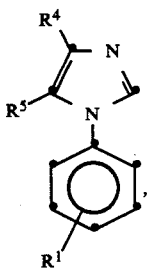

(I)

wherein
$R^1$ represents hydrogen or halogen in the o-, m- or p-position, and the halogen can occur once or repeatedly in the phenyl radical,
$R^4$ represents

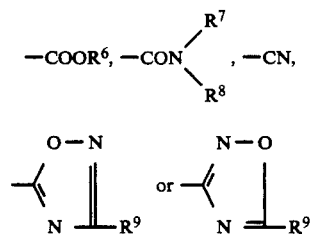

with $R^6$ and $R^9$ representing hydrogen or alkyl of 1 to 6 carbon atoms, $R^7$ and $R^8$ are the same or different and represent hydrogen or alkyl of 1 to 6 carbon atoms or $R^7$ and $R^8$ together with the nitrogen atom represent a saturated heterocyclic five-membered or six-membered ring optionally containing another heteroatom which is O or N, and
$R^5$ represents hydrogen, alkyl of 1 to 6 carbon atoms or $C_{1-4}$-alkoxy-$C_{1-4}$-alkyl.

2. 1-(3-chlorophenyl)-imidazole-4-carboxylic acid ethyl ester,
1-(3,4-dichlorophenyl)-imidazole-4-carboxylic acid ethyl ester,
1-(4-chlorophenyl)-imidazole-4-carboxylic acid ethyl ester,
1-(4-fluorophenyl)-imidazole-4-carboxylic acid ethyl ester,
1-(3-chlorophenyl)-imidazole-4-carboxylic acid isopropyl ester,
1-(4-fluorophenyl)-imidazole-4-carboxylic acid isopropyl ester,
1-(3-chlorophenyl)-imidazole-4-carboxylic acid or
1-(4-fluorophenyl)-imidazole-4-carboxylic acid each a compound of claim 1.

3. 1-(3-chlorophenyl)-imidazole-4-carboxylic acid diethylamide,
1-(4-fluorophenyl)-imidazole-4-carboxylic acid diisopropylamide, or
1-(3-chlorophenyl)-5-methyl-imidazole-4-carboxylic acid amide each a compound of claim 1.

4. 1-(3-chlorophenyl)-4-(3-ethyl-1,2,4-oxadiazol-5-yl)-imidazole,
1-(3,4-dichlorophenyl)-4-(3-ethyl-1,2,4-oxadiazol-5-yl)-imidazole,
1-(4-chlorophenyl)-4-(3-ethyl-,1,2,4-oxadiazol-5-yl)-imidazole,
1-(4-fluorophenyl)-4-(3-ethyl-1,2,4-oxadiazol-5-yl-imidazole,
1-(3-bromophenyl)-4-(3-ethyl-1,2,4-oxadiazol-5-yl)-imidazole,
1-(3-chlorophenyl)-4-(3-ethyl-1,2,4-oxadizol-5-yl)-5-methyl-imidazole,
1-(3-chlorophenyl)-4-(5-ethyl-1,2,4-oxadiazol-3-yl)-5-methyl-imidazole, or
1-(3-chlorophenyl)-4-(3-ethyl-1,2,4-oxadiazol-5-yl)-5-methoxy-methyl-imidazole each a compound of claim 2.

5. 1-(3-chlorophenyl)-imidazole-4-carbonitrile,
1-(3-chlorophenyl)-5-methyl-imidazole-4-carbonitrile or
1-(4-fluorophenyl)-5-methyl-imidazole-4-carbonitrile each a compound of claim 1.

6. An imidazole of the formula

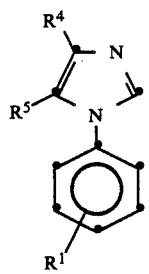

wherein
$R^1$ represents hydrogen or halogen in the o-, m- or p-position, and the halogen can occur once or repeatedly in the phenyl radical,
$R^4$ represents

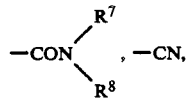

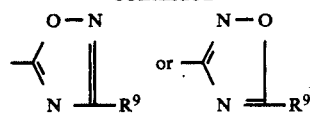

with $R^9$ representing hydrogen or alkyl of 1 to 6 carbon atoms, $R^7$ and $R^8$ are the same or different and represent hydrogen or alkyl of 1 to 6 carbon atoms or $R^7$ and $R^8$ together with the nitrogen atom represent a saturated heterocyclic five-membered or six-membered ring optionally containing another heteroatom which is O or N, and $R^5$ represents hydrogen, alkyl of 1 to 6 carbon atoms or $C_{1-4}$-alkoxy–$C_{1-4}$-alkyl.

* * * * *